US012806307B2

(12) United States Patent
Grunlan et al.

(10) Patent No.: US 12,806,307 B2
(45) Date of Patent: Nov. 24, 2026

(54) SHAPE MEMORY POLYMER SCAFFOLDS WITH TUNABLE TRANSITION TEMPERATURES TO TREAT TISSUE DEFECTS

(71) Applicant: The Texas A&M University System, College Station, TX (US)

(72) Inventors: Melissa A. Grunlan, College Station, TX (US); Michaela R. Pfau-Cloud, Long Lake, MN (US); Courteney T. Roberts, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 737 days.

(21) Appl. No.: 18/131,188

(22) Filed: Apr. 5, 2023

(65) Prior Publication Data

US 2023/0321318 A1 Oct. 12, 2023

Related U.S. Application Data

(60) Provisional application No. 63/327,797, filed on Apr. 6, 2022.

(51) Int. Cl.
*C08G 63/08* (2006.01)
*A61L 24/04* (2006.01)

(52) U.S. Cl.
CPC ............ *A61L 24/046* (2013.01); *C08G 63/08* (2013.01)

(58) Field of Classification Search
CPC combination set(s) only.
See application file for complete search history.

(56) References Cited

U.S. PATENT DOCUMENTS

2014/0025161 A1* 1/2014 Stankus .................... A61F 2/86 623/1.19
2017/0021060 A1* 1/2017 Grunlan .................. A61L 27/18
2021/0244854 A1* 8/2021 Biris ....................... A61L 27/24

* cited by examiner

*Primary Examiner* — Peter A Salamon
(74) *Attorney, Agent, or Firm* — Jackson Walker LLP

(57) ABSTRACT

In an embodiment, the present disclosure pertains to method of forming a shape memory polymer (SMP) scaffold. In general, the method includes preparing a salt template, preparing a macromer and/or polymer solution having at least one macromer or polymer, preparing a photoinitiator solution having at least one photoinitiator, adding the macromer and/or polymer solution and the photoinitiator solution to the salt template, exposing the salt template to ultraviolet light, removing the salt template, and forming an SMP scaffold. In some embodiments, the at least one macromer or polymer has at least one star configuration. In an embodiment, the present disclosure pertains to an SMP scaffold having at least one macromer, polymer, or photoinitiator to crosslink a polymer. In some embodiments, the at least one macromer or polymer has a star configuration. The SMP scaffold can be formed via solvent-casting/particulate leaching, electrospinning, additive manufacturing, and combinations thereof.

11 Claims, 6 Drawing Sheets

SHAPE MEMORY POLYMER SCAFFOLDS WITH TUNABLE TRANSITION TEMPERATURES TO TREAT TISSUE DEFECTS

CROSS-REFERENCE TO RELATED APPLICATIONS

This patent application claims priority from, and incorporates by reference the entire disclosure of, U.S. Provisional Patent Application No. 63/327,795 filed on Apr. 6, 2023.

STATEMENT REGARDING FEDERALLY SPONSORED RESEARCH

This invention was made with government support under 1R01DE025886-01A1 and 1R03AG067140-01A1 awarded by the National Institutes of Health (NIH). The government has certain rights in the invention.

TECHNICAL FIELD

The present disclosure relates generally to shape memory polymer scaffolds and more particularly, but not by way of limitation, to shape memory polymer scaffolds with tunable transition temperatures to treat tissue defects.

BACKGROUND

This section provides background information to facilitate a better understanding of the various aspects of the disclosure. It should be understood that the statements in this section of this document are to be read in this light, and not as admissions of prior art.

"Self-fitting" shape memory polymer (SMP) scaffolds based on crosslinked linear-poly(ε-caprolactone)-diacrylate (linear-PCL-DA, $M_n$~10 k g mol$^{-1}$) were prepared as networks (i.e., 100 wt % PCL), and also as semi-interpenetrating networks (semi-IPNs) with crosslinked linear-PCL-DA ($M_n$~10 k g mol$^{-1}$) and linear-poly(L-lactic acid) (PLLA, $M_n$~15 k g mol$^{-1}$) [75/25 wt %]. The semi-IPN scaffolds were more mechanically robust (e.g., higher elastic modulus) and exhibited accelerated degradation rates versus linear-PCL-DA ($M_n$~10 k g mol$^{-1}$) scaffolds. However, their potential to treat irregular craniomaxillofacial (CMF) bone defects as well as other bone defects is limited by their relatively high fitting temperature ($T_{fit}$~55° C.; corresponding to the $T_m$ of PCL) required for shape recovery (i.e., expansion) and subsequent shape fixation during press fitting of the scaffold, which can be harmful to surrounding tissue beyond certain amounts of exposure time. (Herein, the $T_m$ of the scaffold is defined in terms of an onset and midpoint of this thermal transition as observed by differential scanning calorimetry [DSC]. Unless noted otherwise, "$T_m$" refers to the midpoint of the $T_m$ range.) Thus, a scaffold exhibiting a $T_m$<~55° C. (but greater than ~37° C.) would afford fitting at more tissue-safe temperatures, including exposure to heat during fitting to prolong working time. In some cases, shape expansion may be desired to be triggered by implantation (i.e., $T_m$~37° C.), thereby requiring a $T_m$ of 37° C. or lower. Additionally, the viscosity of the solvent-based precursor solutions (i.e., containing the macromers and/or polymers as well as other components), cast over a fused salt template during fabrication, can limit scaffold size that can be produced. Thus, reducing the viscosity of the precursor solution would be helpful.

Previous literature has indicated that $T_m$ of linear-PCL is "tunable" with molecular weight. For example, the $T_m$ of linear-PCL is reported to be tuned from ~60 to ~43° C. as the number average molecular weight ($M_n$) is decreased. However, such tunability was not realized in recent studies. For instance, linear-PCL$_n$-DA (n=90; $M_n$~10 k g mol$^{-1}$) and linear-PCL$_n$-DA (n=50; $M_n$~5600 g mol$^{-1}$) were formed as crosslinked films. However, only a slight $T_m$ reduction was seen for films based on "n=50" ($T_m$~49° C.) as compared to those based on "n=90" ($T_m$~55° C.). Moreover, a $T_m$ was not achieved in the lower targeted range (~50 to ~37° C., or lower). Porous scaffolds prepared from linear-PCL$_n$-DA (n=50; $T_m$~55° C.) versus linear-PCL$_n$-DA (n=90; $T_m$~56° C.) likewise lacked an appreciable reduction of $T_m$ and $T_m$'s in the targeted range were not achieved.

In contrast, as disclosed herein, star-PCL-tetraacrylates (TAs) (i.e., PCL macromers with a 4-arm star architecture) were very effective at reducing the $T_m$, and systematically lowering the $M_n$ afforded reduced $T_m$'s in the targeted range. Scaffolds prepared from star-PCL-TA ($M_n$~10 k g mol$^{-1}$) exhibited a $T_{m,onset}$ of ~43° C. and $T_{m,midpoint}$ of ~49° C. as compared to scaffolds prepared from linear-PCL-DA ($M_n$~10 k g mol$^{-1}$) ($T_{m,onset}$~51° C. and $T_{m,midpoint}$ of ~56° C.) (i.e., a ~8° C. decrease), despite the macromers being of the same total $M_n$. $T_m$ values were further reduced for scaffolds prepared from star-PCL-TA ($M_n$~7.5 k g mol$^{-1}$) ($T_{m,onset}$~34° C. and $T_{m,midpoint}$ of ~40° C.) and star-PCL-TA ($M_n$~5 k g mol$^{-1}$) ($T_{m,onset}$~18° C. and $T_{m,midpoint}$ of ~29° C.). Thus, in the present disclosure, network and semi-IPN SMP scaffolds were formed with a 4-arm star-PCL-TA ($M_n$~10 k g mol$^{-1}$) and, in the case of semi-IPNs, with either linear-PLLA ($M_n$~15 k g mol$^{-1}$) or star-PLLA ($M_n$~15 k g mol$^{-1}$). Analogous scaffolds were formed with linear-PCL-DA ($M_n$~10 k g mol$^{-1}$). In total, four semi-IPN compositions were prepared: linear-PCL-DA/linear-PLLA (L/L), linear-PCL-DA/star-PLLA (L/S), star-PCL-TA/linear-PLLA (SIL) and star-PCL-TA/star-PLLA (S/S). For these semi-IPNs, the wt % ratio of the two components was 75:25 ("PCL": "PLLA"). Two PCL network scaffolds were also prepared: LPCL (i.e., 100% linear-PCL-DA) and SPCL (i.e., 100% star-PCL-TA). The S/S semi-IPN scaffold exhibited particularly notable properties. In addition to achieving a lower, tissue-safe $T_m$ ($T_{m,onset}$~40° C. and $T_{m,midpoint}$ of ~50° C.), it exhibited the fastest rate of degradation which is anticipated to more favorably permit neotissue infiltration. The radial expansion pressure exerted by the S/S semi-IPN scaffold at ~45° C. was greater than that of LPCL at ~55° C.; this is expected to enhance osseointegration and mechanical stability. The intrinsic viscosity of the S/S semi-IPN macromer solution was also reduced, facilitating the production of larger scaffold specimens.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to method of forming a shape memory polymer (SMP) scaffold. In general, the method includes preparing a salt template, preparing a macromer and/or polymer solution having at least one macromer or polymer, preparing a photoinitiator solution having at least one photoinitiator, adding the macromer and/or polymer solution and the photoinitiator solution to the salt template, exposing the salt template to ultraviolet (UV) light, removing the salt template, and forming an SMP scaffold. In some embodiments, the at least one macromer or polymer has at least one star configuration.

In an embodiment, the present disclosure pertains to an SMP scaffold having at least one macromer, polymer, or photoinitiator to crosslink a polymer. In some embodiments, the at least one macromer or polymer has a star configuration. In some embodiments, the SMP scaffold is formed via a method that can include, without limitation, solvent-casting/particulate leaching (SCPL), electrospinning, additive manufacturing, and combinations thereof.

BRIEF DESCRIPTION OF THE DRAWINGS

A more complete understanding of the subject matter of the present disclosure may be obtained by reference to the following Detailed Description when taken in conjunction with the accompanying Drawings wherein:

FIG. 2(A) illustrates linear-PCL-based, FIG. 2(B) illustrates star-PCL-based scaffolds, and FIG. 2(C) illustrates mass loss at 72 h for all scaffold compositions; *p<0.05, **p<0.01, #p>0.05.

FIG. 4 illustrates radial expansion pressure tested at $T_{fit}$; *p<0.05, **p<0.01.

DETAILED DESCRIPTION

Figure 1A:
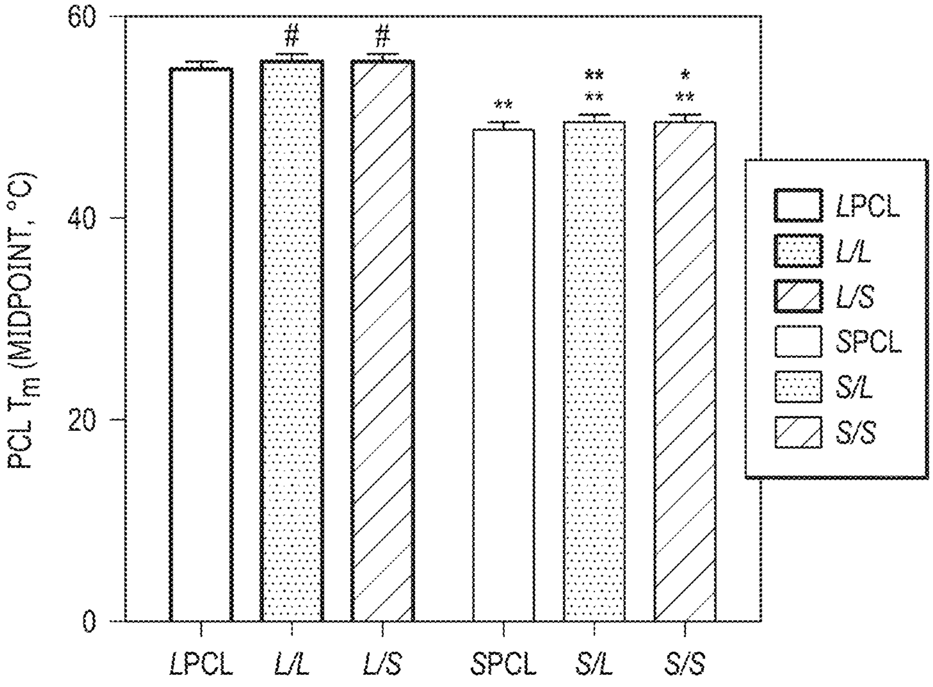
FIG. 1(A) Midpoint $T_m$ of PCL of scaffolds; *p<0.05, p<0.01, #p>0.05. Note: the black color-coded statistics are comparisons to LPCL and blue color-coded statistics are comparisons to SPCL.

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

It should be noted that, as used herein, the star configuration (i.e., architecture), is broadly defined as linear "arms" (3 or more) emanating from a central "core". Furthermore, as used herein, "macromer" refers to polymeric species having crosslinkable moieties such as acrylates (e.g., linear-PCL-DA and star-PCL-TA) whereas "polymer" refers to polymeric species lacking in crosslinkable moieties (e.g. linear-PLLA and star-PLLA).

Shape memory polymer (SMP) scaffolds can be used to treat a variety of tissue defects that often have irregular geometrics. Disclosed herein are SMP scaffolds whose transition temperature ($T_{trans}$) can be tuned and that can conformally fill tissue defects via shape recovery. This is afforded by preparing PCL with a star architecture and tuning the molecular weight. As a result of changes to % crystallinity, the melt transition temperature ($T_m$) is tuned such that $T_m$ decreases with decreasing % crystallinity. This $T_m$ represents the $T_{trans}$ of the scaffold, which is the temperature at which the scaffold becomes malleable and also undergoes shape recovery for tissue defect filling. In this way, a scaffold at or above its $T_m$ will undergo conformal, self-fitting into a tissue defect via expansion (i.e., shape recovery). If $T_m$ is greater than body temperature, the scaffold would be warmed via exposure to sufficiently warm (i.e., temperatures approximately equal to or greater than $T_{trans}$) air, water, saline, or other liquids before and/or during placement into tissue defects. Following expansion, and cooling to body temperature, the scaffold will return to a relative rigid state and the new shape fixed within the defect. If $T_{trans}$ is approximately that of body temperature, shape recovery may alternatively be triggered by implantation into the body alone. Prior to implantation into a tissue defect, the scaffold may be shape fixed in a temporary, relatively compressed shape to afford ease of delivery/insertion/implantation, including via needle, catheter, grafting tool, and the like. Prepared from biodegradable PCL-based systems, the scaffolds are bioresorbable (in part or in full). Thus, if fully bioresorbable, they do not require surgical removal. Scaffolds are prepared via solvent-casting/particulate leaching (SCPL) but may be formed through other processes (e.g., electrospinning or additive manufacturing). PCL may be combined with other monomers, polymers, or macromers as well as fillers to tune mechanical, degradation, surface, and other properties. Coatings may also be applied. Scaffolds may be combined with exogeneous cells, exogeneous growth factors, or other biomolecules.

The SMP scaffolds are composed of polymers and may optionally include fillers and coatings. Optionally, exogenous cells and/or exogeneous growth factors may be introduced before or during implantation. The polymer is exclusively or partly based on PCL for shape memory behavior. The PCL is of a star architecture, typically having three or more arms emanating from a central core. It is generally also crosslinkable and typically terminated with acrylate groups. For instance, 4-armed star-PCL-tetrols can be acrylated to produce 4-armed star-PCL-TA. Scaffolds may optionally include other polymers, copolymers, and the like, such as other polyesters (e.g., poly(L-lactic acid), poly(glycolic acid), and copolymers), and other polymers (e.g., poly(dimethylsiloxane), and poly(propylene fumarate)) incorporated in a variety of ways to form various network types (e.g., co-networks, interpenetrating polymer networks (IPNs), and semi-IPNs). Fillers (e.g., bioglass, tricalcium phosphate, hydroxyapatite, silicates, etc.) may be incorporated into the scaffold. A coating may be applied to the scaffold (e.g., polydopamine, or collagen). Scaffolds may optionally be combined with exogenous cells and growth factors before or during implantation.

Tuning the $T_m$ of SMP scaffolds via the use of star-PCL is novel. This achieves tunable, and lower $T_m$ values versus for those based on linear-PCL. Previously, SMP scaffolds were prepared from linear-PCL-DA ($M_n$~10 k g $mol^{-1}$) and had a $T_m$ of ~56° C. This requires warming to ~56° C. Reducing the scaffold $T_m$ as described herein allows lower temperatures to be used for fitting of such scaffold into tissue defects. In this way, the scaffold could be exposed to reduced temperatures prior to placing into defects, improving safety for the surgeon, and reducing heat exposure to tissues. As such, to extend working time, it could also be irrigated with warm saline or otherwise warmed with reduced heat exposure to tissue. Furthermore, if the $T_m$ was reduced to ~37° C. or below, scaffolds would expand upon implantation due to body temperature (i.e., without the application of warm saline, etc.). In this way, SMP scaffolds with tunable, and reduced $T_m$ values improve efficacy and utility.

Working Examples

Reference will now be made to more specific embodiments of the present disclosure and data that provides support for such embodiments. However, it should be noted that the disclosure below is for illustrative purposes only and is not intended to limit the scope of the claimed subject matter in any way.

A major limitation of biologic and alloplastic grafts used to treat irregularly shaped craniomaxillofacial (CMF) bone defects or other bone defects is the difficulty in achieving sufficient bone-to-graft contact, essential for osseointegration and healing. Auto-grafting remains the clinical "gold standard", but in addition to the demands of surgical harvesting, bone graft rigidity contributes to poor shaping and tissue contact, ultimately leading to graft resorption. Synthetic bone graft substitutes, including ceramic injectables and bone cements, utilize in situ curing to achieve a defect-specific fit. However, they are limited by risks associated with brittle mechanical properties (leading to post-surgical fracture), exothermic curing (leading to tissue damage), and shrinkage post-cure (leading to poor bone-to-graft contact). PEEK implants can be formed with patient-specific geometry via 3D printing, but are non-regenerative. Thus, an off-the-shelf regenerative scaffold material that can readily achieve conformal fit into irregular CMF bone defects is expected to improve healing outcomes.

"Self-fitting" scaffolds based on thermoresponsive shape memory polymers (SMPs) as a regenerative approach to treat CMF bone defects have previously been reported. Porous SMP scaffolds were prepared from linear-PCL-DA ($M_n$~10 k g $mol^{-1}$) by photocuring a solvent-based macromer solution over a fused salt template followed by aqueous extraction of the template (i.e., solvent-casting/particulate leaching, SCPL). For such PCL SMP scaffolds, covalent cross-links act as netpoints and PCL lamellae act as switching segments. In a surgical setting, the PCL scaffolds could be warmed in saline to their "fitting temperature" ($T_{fit}$~55° C., related to $T_{m,PCL}$), causing the PCL lamellae to begin to melt and the scaffold to subsequently soften. It could thus be readily press-fit into the defect site as shape recovery would drive expansion of the scaffold to the perimeter. Then, as the scaffold would cool to body temperature ($T<T_{fit}$), the PCL lamellae would re-crystallize and return the scaffold to its relatively rigid state with the scaffold fixed into the shape of the defect. Importantly, the PCL SMP scaffolds displayed high shape fixity and recovery, non-brittle mechanical properties, and high pore interconnectivity. Increasing the rigidity of the PCL scaffolds would improve structural support in the early stages of healing and increasing the rate of degradation would promote osseointegration and regeneration. Thus, thermoplastic linear-PLLA (~15 k g $mol^{-1}$) was incorporated into thermoset linear-PCL-DA (~10 k g $mol^{-1}$) networks to yield linear-PCL-DA/linear-PLLA semi-interpenetrating network (semi-IPN) scaffolds. A semi-IPN scaffold prepared with 75/25 wt % PCL/PLLA maintained SMP behavior ($T_{fit}$~55° C.), but demonstrated an increased modulus and accelerated degradation rate compared to the linear-PCL-DA control. The faster degradation of the linear-PCL-DA/linear-PLLA semi-IPNs was linked to polymer phase separation. Likewise, phase separation has been shown to impact mechanical and degradation properties of polyester blends.

Further improvements to mechanical and degradation properties of PCL-based SMP scaffolds, as well as reducing the $T_{fit}$ (to avoid possible tissue damage) and reducing macromer solution viscosity (to aid in scaffold fabrication), would be a significant enhancement in their utility. Because of their unique degradative, mechanical, and rheological properties, star-polymer or star-macromer analogues may offer distinct advantages to the linear-PCL-DA/linear-PLLA semi-IPN scaffolds. Star-polymers are notably associated with reduced hydrodynamic volumes which affects dispersion and interfacial macromolecular interactions. Thus, star-polymers have been used to improve miscibility and resulting toughness of blends and polymer nanocomposites. Moreover, star-polymers are well known for having reduced dilute solution viscosities due to less chain entanglements relative to their linear counterparts. In the fabrication of SMP scaffolds, during solvent casting of the macromer solution over a fused salt template, use of star-polymers and/or star-macromers this could aide in solution diffusion such that larger scaffold specimens could be readily prepared.

Herein, towards favorable tuning of PCL scaffold and PCL/PLLA semi-IPN scaffold properties, the impact of a crosslinkable 4-arm star-PCL macromer analogue was assessed. Specifically, scaffold compositions were systematically made with combinations of linear-PCL-DA or star-PCL-TA and linear-PLLA or star-PLLA: linear-PCL-DA/linear-PLLA (L/L), linear-PCL-DA/star-PLLA (L/S), star-PCL-TA/linear-PLLA (S/L) and star-PCL-TA/star-PLLA. The ratio of PCL/PLLA was maintained at 75/25 wt %, that of the L/L semi-IPN previously shown to best enhance compressive modulus and degradation rate versus the linear-PCL-DA scaffold (LPCL) (i.e., 100% linear-PCL-DA). In addition to the LPCL scaffold, a star-PCL-TA scaffold (SPCL) (i.e., 100% star-PCL-TA) was also prepared. All scaffolds were prepared with the same SCPL protocol to generate scaffolds with similar pore size and interconnectivity. The resulting SMP scaffolds were assessed for their thermal, degradative, mechanical, and shape memory properties. The solution viscosity of macromer solutions used in the SCPL fabrication process was also examined and select compositions were used to fabricate scaffolds with larger dimensions.

Materials

Linear-PCL-diol ($M_n$=10 k g $mol^{-1}$ per manufacturer specifications), 4-(dimethylamino)pyridine (DMAP), triethylamine ($Et_3N$), acryloyl chloride, potassium carbonate ($K_2CO_3$), anhydrous magnesium sulfate ($MgSO_4$), sodium chloride (NaCl, salt), (3S)-cis-3,6-dimethyl-1,4-dioxane-2,5-dione (L-lactide), ε-caprolactone, pentaerythritol, tin(II) 2-ethylhexanoate ($Sn(Oct)_2$), ethylene glycol, 2,2-dimethoxy-2-phenyl acetophenone (DMP), 1-vinyl-2-pyrrolidinone (NVP), sodium hydroxide (NaOH), deuterated chloroform ($CDCl_3$), and solvents were purchased from Sigma-Aldrich. All solvents and ethylene glycol were dried over 4 Å molecular sieves, all reagents were vacuum dried overnight (ON), and all glassware and stir bars were dried at 120° C. ON prior to use. Salt was sieved using an ASTM E-11 no. 40 and no. 35 sieves with 425 mm and 500 mm openings respectively; scanning electron microscopy (SEM) and ImageJ showed an average salt size of 460±70 mm.

Methods

Syntheses. All reactions were run under a nitrogen ($N_2$) atmosphere with a Teflon-covered stir bar. Following purification, polymer structures (including % acrylation, architecture, and $M_n$) were confirmed with 1H NMR spectroscopy (Inova 500 MHz spectrometer in FT-mode with $CDCl_3$ as the standard). Polymer thermal properties were determined using differential scanning calorimetry (DSC, TA Instruments Q100) as described below.

Thermoplastic linear- and star-PLLA ($M_n$~15 k g mol$^{-1}$) were synthesized via ring opening polymerizations (ROPs) according to an established protocol. L-Lactide (6.0 g), alcohol initiator, and $Sn(Oct)_2$ catalyst were allowed to react ON at 120° C. The alcohol initiator was varied from difunctional ethylene glycol to tetrafunctional pentaerythritol to achieve a linear- and star-PLLA architecture, respectively. $M_n$ was controlled via molar equivalence of monomer to initiator (104:1, [M]:[I]). The crude products were dissolved in a minimal amount of chloroform and were precipitated into methanol. Final products were filtered and vacuum dried (RT, ON, 30 in. Hg) to obtain purified linear- and star-PLLA. Target $M_n$ and architecture were verified using 1H NMR end group analysis (CH d=5.2 ppm in repeat unit compared to terminal CH d=3.7 ppm). The following thermal transitions were observed for linear-PLLA [$T_g$=45° C., $T_m$=155° C., 50% crystallinity] and star-PLLA [$T_g$=49° C., $T_m$=152° C., 15% crystallinity]. Table 1 below illustrates thermal properties from DSC and $M_n$ from NMR.

TABLE 1

Summary of thermal properties

| | DSC | | | NMR |
|---|---|---|---|---|
| | $T_g$(° C.) | $T_m$(° C.) | % Crystallinity | $M_n$ (kg/mol) |
| Linear-PLLA-diol | 45.1 ± 0.90 | 155 ± 0.36 | 49.8 ± 0.56 | 15.6 |
| Star-PLLA-tetrol | 49.2 ± 0.54 | 152 ± 0.47 | 15.0 ± 1.9 | 14.7 |

Star-PCL-tetrol was synthesized via ROP (analogous to that described above) with a target $M_n$ of ~10 k g mol$^{-1}$ to match that of linear-PCL-diol ($M_n$=10 k g mol$^{-1}$; Sigma-Aldrich). The ε-caprolactone (25.0 g), pentaerythritol (88:1, [M]:[I]) and $Sn(Oct)_2$ were combined and were allowed to react ON at 120° C. The crude product was re-dissolved and precipitated as described above to yield purified star-PCL-tetrol. The target $M_n$ and architecture were verified via 1H NMR end group analysis ($CH_2$ d=4.1 ppm in repeat unit compared to terminal $CH_2$ d=3.7 ppm). Thermal transitions were determined for both the linear-PCL-diol [$T_g$=65° C., $T_m$=53° C., 48% crystallinity] and the star-PCL-tetrol [$T_g$=63° C., $T_m$=50° C., 45% crystallinity]. Table 2 below illustrates thermal properties from DSC and $M_n$ from NMR.

TABLE 2

Summary of thermal properties

| | DSC | | | NMR |
|---|---|---|---|---|
| | $T_g$(° C.) | $T_m$(° C.) | % Crystallinity | $M_n$ (kg/mol) |
| Linear-PLLA-diol | −65.1 ± 0.90 | 52.7 ± 0.36 | 47.7 ± 0.56 | 10.3 |
| Star-PLLA-tetrol | −63.2 ± 0.54 | 50.0 ± 0.47 | 44.8 ± 1.6 | 10.9 |

Linear-PCL-diol and star-PCL-tetrol were acrylated to form photo-crosslinkable linear-PCL-DA and star-PCL-TA macromers, respectively, using established acrylation protocols. Briefly, linear-PCL-diol (20.0 g, 2.0 mmol) was combined with DMAP (6.6 mg) serving as the catalyst and they were dissolved in dichloromethane (DCM, 0.17 g mL-1). After purging with $N_2$, triethylamine (4.0 mmol) and acryloyl chloride (8.0 mmol) were added to the flask and the reaction was left to stir at RT for 30 min. An analogous procedure was followed for the star-PCL-tetrol but molar ratios were doubled to account for the 4 end groups [DMAP=13.2 mg, triethylamine=8.0 mmol, acryloyl chloride=16.0 mmol]. Established work-up procedures were followed to obtain linear-PCL-DA and star-PCL-TA. Percent acrylation was confirmed via 1H NMR end group analysis ($CH_2$ d=4.1 ppm in repeat unit, compared to acrylate protons CH=$CH_2$ d=5.6, 6.1 and 6.4 ppm) to be 485% for both linear-PCL-DA and star-PCL-TA. NMR % acrylation for Linear-PCL-DA was 93.4% and for Star-PCL-TA was 87.4%.

Fabrication

Scaffolds. Porous scaffolds were prepared via SCPL, based on a previous report, employing a fused salt template for pore interconnectivity. Sieved NaCl (10.0 g, 460±70 mm) was placed in a 20 mL scintillation vial (I.D.=25 mm) and DI water (7.5 wt %) was added in four portions followed by manual stirring with a spatula after each addition. The wet salt was pressed with a glass rod and the vials were centrifuged (15 min, 3220×g). The opened vials were air dried for ~1 h and were subsequently vacuum dried (RT, ON, 30 in. Hg).

Next, macromer solutions were prepared by dissolving a designated macromer or combination of two macromers (75/25 wt % ratio) in DCM (0.15 g total per mL DCM). Photoinitiator solution (10 wt % DMP in NVP) was then added at 15 vol %. To each salt template ~5 mL of macromer solution was added and the vials were centrifuged (10 min, 1260×g) to promote macromer solution diffusion throughout the template. To crosslink acrylated macromers, opened vials were then exposed to UV light for 5 min (UV-Transilluminator, 6 mW cm$^{-2}$, 365 nm) followed by air drying in a fume hood ON. To remove the salt template, vials were then placed in a solution of water and ethanol (1:1 by vol.) for ~5 days with daily solution changes. Resulting porous scaffolds were air dried ON, and finally heat treated (170° C., 10 min, 30 in. Hg). The dried scaffolds (d~12 mm) were sliced into three specimens (t~2 mm) (Vibratome, Leica VT 1000 S) and were biopsy punched (Integra Miltex, 6 mm). Final specimen dimensions were d~6 mm×t~2 mm.

Solid films. Analogous solid films of each scaffold composition were prepared for % porosity calculations and to evaluate polymer miscibility in film cross-sections. A macromer solution (25 wt % total polymer in DCM), combined with the aforementioned photoinitiator solution (15 vol %), was added to a circular silicone mold (d~45 mm×t~2 mm; McMaster-Carr) secured between 2 glass slides. The mold was then exposed to UV-light (UV Transilluminator, 6 mW cm 2, 365 nm) for 3 min on each side. The swollen films were air dried ON followed by vacuum drying (RT, 4 h, 30 in. Hg), soaking in ethanol while placed atop a shaker table (150 rpm, 3 h), air drying ON, and finally, were heat treated (170° C., 30 min, 30 in. Hg). Films were punched to form disc specimens (d~5 mm×t~1.1 mm) used for testing.

Scaffold sol content. Scaffolds (d~6 mm×t~2 mm; N=3) were each submerged in 10 mL of DCM in a scintillation vial. Sealed vials were placed atop a shaker table (150 rpm, 48 h) and scaffolds were subsequently rinsed with DCM, air dried, and dried under vacuum (RT, ON, 30 in. Hg). Initial and final mass values were used to calculate % sol content.

Thermal gravimetric analysis (TGA). TGA (TA Instruments Q50) of scaffolds (~10 mg; N=1) was performed under $N_2$ from RT to 500° C. (heating rate=10° C. $min^{-1}$) using platinum pans.

% Porosity. The percent porosity of scaffolds (N=3) was determined gravimetrically using equation (1):

$$\text{Porosity } (\%) = \frac{\rho_{solid\ film} - \rho_{porous\ scaffold}}{\rho_{solid\ film}} * 100 \quad (1)$$

where $\rho_{porous\ scaffold}$ is the density of the final scaffold specimens and $\rho_{solid\ film}$ is the density of analogous solid film samples.

Pore size. Scaffold pore interconnectivity and pore size were evaluated with SEM (JEOL JCM-5000 Neoscope, accelerating voltage ~10 kV) following coating with Au—Pt (~4 nm). Scaffold images (N=4) were analyzed using image analysis software (Image J); measurements (N=30) were taken from pores along the diagonal midline to determine average pore size.

Thermal transitions and % crystallinity. Differential scanning calorimetry (DSC; TA Instruments Q100) was used to determine $T_g$, $T_m$, and % crystallinity of PCL and PLLA prior to scaffold fabrication. Specimens (~10 mg; N=3) were sealed in hermetic pans and heated at a rate of 10° C. $min^{-1}$, and values were taken from the second cycle to erase thermal history. The onset and midpoint of $T_{m,PCL}$ and $T_{m,PLLA}$ was determined using TA Universal Analysis software from the onset and the maximum of the endothermic melt peak, respectively. Percent crystallinity was determined with equation (2):

$$\%\chi_c = \frac{\Delta H_m - \Delta H_c}{\Delta H_m^{\circ}} * 100 \quad (2)$$

where $\Delta H_m$ is the enthalpy of fusion taken from the integral of the endothermic melt peak, $\Delta H_c$ is the enthalpy of crystallization from the exothermic cold crystallization peak and $$\Delta H_m^{\circ}$$

is the theoretical value for 100% crystalline PCL (139.5 J $g^{-1}$) or PLLA (93.0 J $g^{-1}$).

Scaffolds (N=3) were likewise examined but using a heating rate of 5° C. min-1 and using the first cycle to examine the impact of fabrication. For semi-IPNs (PCL/PLLA 75/25 wt %), a correction factor to account for polymer wt % was included in % crystallinity calculations according to equation (3):

$$\%\chi_c = \frac{\Delta H_m - \Delta H_c}{\Delta H_m^{\circ} * w} * 100 \quad (3)$$

where w is the mass fraction of the designated polymer species (i.e. w=0.75 for PCL and w=0.25 for PLLA in semi-IPN compositions).

Degradation. Degradation tests were performed under base-catalyzed conditions (0.2 M NaOH) according to ASTM F1635. Scaffold specimens (d~6 mm×t~2 mm; N=3 per time point) were each submerged in 10 mL of the basic solution in a sealed glass vial and maintained in an incubator (VWR Benchtop Shaking Incubator Model 1570) at 37° C. and 60 rpm. At each of the five designated time points (24, 48, 72, 120, and 168 h), samples were removed, thoroughly rinsed with DI water, blotted, and finally dried under vacuum (RT, ON, 30 in. Hg). Specimen mass was measured to examine gravimetric mass loss.

Compressive mechanical properties. Scaffold specimens (d~6 mm×t~2 mm; N=3) underwent static compression testing (Instron 5944) at RT. Specimens were subjected to a constant strain (1.5 mm $min^{-1}$) up to 85% strain. Due to their non-brittle nature, no specimen fractured. The average compressive modulus (E), strength (CS), and toughness were reported: E was determined from the initial linear region (≤10% ε). CS was determined from the stress at 85% strain. Toughness values were calculated from the area of the stress-strain curves up to 85% strain.

Shape memory properties. Self-fitting behavior in model defect. Scaffold specimens (d~6 mm×t~2 mm; N=3) were evaluated for their "self-fitting" ability using a model defect representative of a rat calvarial defect. From an ultra-high-molecular-weight polyethylene (UHMWPE) sheet (McMaster-Carr, t~2 mm), a circular defect (d~5 mm) was created with a drill press (Grizzly G7948). A "fitting temperature" ($T_{fit}$) was determined as the saline temperature that, after 1 min of submersion, consistently produced a scaffold that was malleable to the touch. A hot plate equipped with a digital temperature probe (Heidolph, MR HEI-TEC) was used to the warm saline in 1° C. intervals within a given scaffold's onset to midpoint $T_{m,PCL}$ range (i.e., 50-56° C. for linear-PCL-based and 42-50° C. for star-PCL-based scaffolds). $T_{fit}$ was determined to be ~55° C. (for linear-PCL-based scaffolds) and ~45° C. (for star-PCL-based scaffolds). Next, each scaffold specimen was subjected to the following protocol: (1) submerged into saline previously heated to the designated $T_{fit}$ and maintained for 1 min; (2) removed and immediately press-fitted into a model defect (at RT); (3) maintained in the model defect for 2 min to fix the new temporary shape; (4) removed from the defect (pushing out by hand), allowed to sit for 2 min; (5) re-submerged into the saline bath at $T_{fit}$ for 1 min to elicit shape recovery, removed, allowed to cool at RT for 2 min. At key points during this sequence, the scaffold diameter was measured using electronic calipers to quantify scaffold strain (e). Steps 1-5 were repeated to determine shape fixity ($R_f$) and shape recovery ($R_r$) over a second cycle. From this process, the $R_f$ and shape recovery $R_r$ for the first (N=1) and second (N=2) cycles were calculated, according to equations (4) and (5), respectively:

$$R_f(N) = \frac{\varepsilon_u(N)}{\varepsilon_m} \quad (4)$$

$$R_f(N) = \frac{\varepsilon_m - \varepsilon_p(N)}{\varepsilon_m - \varepsilon_p(N-1)} \quad (5)$$

where $\varepsilon_m$ is the maximum strain following step 2, $\varepsilon_u(N)$ is the strain in the stress-free state following step 3, and $\varepsilon_p$ is the final recovered strain following step 4. Strain values were determined via electronic caliper measurements.

Radial pressure during shape recovery. Scaffold discs (d~6 mm×t~2 mm; N=5) were subjected to radial mechanical testing (Instron 5965 equipped with a Blockwise RJA62 J-Crimp Radial Compression Station), to determine the radial pressure exerted during shape recovery at a scaffold's $T_{fit}$ (LPCL, L/L, L/S at 55° C. and SPCL, S/L, S/S at 45° C.). This was intended to mimic shape recovery during self-fitting of the scaffold specimen into a d~5 mm defect. Specimens were loaded into the bore set to an initial d~6.5 mm at RT. The temperature was then increased to the designated $T_{fit}$ and maintained for 3 min. Next, the bore diameter was reduced from 6.5 mm to 5 mm at a rate of 1 mm $min^{-1}$. Force was monitored throughout the procedure, and total radial force (TRF) was calculated and converted to radial pressure based on exact scaffold dimensions.

Solution Viscosity and Scaffold Scale-Up

Solution viscosity. The complex viscosity [Z*] of each scaffold macromer precursor solutions (N=3) was measured as a function of frequency (100 Hz to 0.1 Hz, Anton Parr MCR 301). Macromer solutions (0.15 g per mL of DCM) were composed of linear-PCL-diol or star-PCL-tetrol (i.e., non-acrylated) and no photoinitiator solution to avoid cross-linking during the test. To determine the intrinsic viscosity, the Z* data was extrapolated to a theoretical zero shear rate (0 Hz).

Solution diffusion through salt template. Select macromer solutions (L/L and S/S), containing dye, were used to assess differences in the rate of diffusion through a salt template. To aide inspection of diffusion, salt templates with a somewhat higher heights were prepared as above but with 15.0 g of sieved salt. Macromer solutions (~7.5 mL) were prepared with designated macromers (i.e., linear-PCL-DA and linear-PLLA or star-PCL-TA and star-PLLA), 15 vol % photoinitiator solution, and a few drops of food coloring. With two salt templates placed side-by-side, each macromer solution was gently poured over the template simultaneously and diffusion captured via video. The process was repeated in triplicate.

Scaled-up scaffold fabrication. The L/L and S/S compositions were again selected to fabricate larger scaffolds due to their lowered solution viscosities. A 5 mm hole (diamond core drill bit, Marshalltown) was drilled into the bottom of a 100 mL beaker (I.D.=43.6 mm) to aid in macromer solution diffusion. Each 100 mL beaker was filled with 50.0 g of salt and 7.5 wt % water was incorporated over 4 additions with mechanical mixing following each addition. A smaller beaker was used to manually push the wet salt down and the salt molds were vacuum dried (RT, 30 in. Hg., ON). Macromer solutions were prepared (~15 mL) according to that described above for fabrication of smaller scaffolds. Once mixed, macromer solution was poured on top of the fused salt mold and was allowed to sit for ~3 min to permit diffusion; aluminum foil covered the beaker to prevent premature UV curing and solvent evaporation. Following UV-cure (InetlliRay 400, 50% intensity) for 10 min, specimens were allowed to dry in a fume hood (48 h) and were then soaked in a 1:1 DI water:ethanol solution with daily solution changes. Dried scaffolds were then annealed and sliced into 2 mm specimens, as described above for the smaller scaffolds. Note, both types of scaffolds were maintained at their full diameter for size comparisons (i.e. no biopsy punch was used). Photos were taken throughout the procedure and low magnification optical microscopy (Leica DM 6B; 5×) was performed on scaffold specimens to broadly examine pore morphology. The procedure was performed in triplicate and scaffolds were measured with electronic calipers to quantify dimensional changes. SEM (JEOL JCM-5000 Neoscope, accelerating voltage ~10 kV, Au—Pt coating ~4 nm) with energy dispersive X-ray spectroscopy (EDS, Oxford Instruments) elemental mapping was also performed to confirm complete porogen leaching from larger constructs.

Statistical analysis. All data was reported as the average±standard deviation. ANOVA tests were performed and if there was a statistical difference, t-tests were performed against the LPCL control. T-tests were also used to make direct comparisons between compositions of interest, which will be specified for each result discussed. For mechanical testing, interquartile range tests were performed and values that were determined as being outliers were removed from the data (final N≥5). For rheology data, linear regression was used to extrapolate complex viscosity to zero shear. Regression analyses were only performed up to 1 Hz to achieve $R^2$ 40.5 and zero shear viscosities were reported as averages±the standard error.

Results and Discussion

Macromer synthesis. Linear- and star-PLLA ($M_n$~15 k g $mol^{-1}$) as well as linear-PCL-diol and star-PCL-tetrol ($M_n$~10 k g $mol^{-1}$) were characterized. Star macromer $M_n$ was selected to match previously studied linear macromers in order to rule out $M_n$ as a variable. As described above, 1H NMR end group analysis was used to determine $M_n$ and confirm architecture (i.e., terminal group protons were approximately doubled for star precursors). DSC was used to determine thermal transitions and % crystallinity, with differences in thermal properties used to further validate precursor architecture. The $T_g$ and $T_m$ values as well as % crystallinity varied for the linear-PLLA ($T_g$~45° C., $T_m$~155° C., ~50%) versus the star-PLLA ($T_g$~49° C., $T_m$~152° C., ~15%) Likewise, differences were observed for the $T_g$, $T_m$, and % crystallinity values of the linear-PCL diol ($T_g$~65° C., $T_m$~53° C., ~48%) and the star-PCL tetrol ($T_g$~63° C., $T_m$~50° C., ~45%).

Subsequently, the linear-PCL diol and star-PCL tetrol were successfully acrylated (>85%) to yield linear-PCL-DA and star-PCL-TA, respectively.

Scaffold fabrication. Fabricated scaffolds were characterized in various ways to ensure effective cross-linking (sol content), to confirm the targeted PCL/PLLA wt % ratio of 75/25 (TGA), and to quantify pore size and % porosity (SEM and density calculations, respectively). Sol content values for 100% PCL scaffolds [LPCL and SPCL] was just 2-4%, further indicating successful cross-linking (i.e., >95%). All semi-IPN scaffolds displayed sol content values <29%, similar to the controls when the thermoplastic PLLA (incorporated at 25 wt %) was considered. Additionally, the TGA thermograms of semi-IPNs all showed ~25 wt % mass loss from 250-350° C. that corresponded to the 25 wt % PLLA contained. Thus, the PLLA did not diminish linear-PCL-DA or star-PCL-TA cross-linking and the targeted 75/25 wt % ratio of PCL/PLLA was maintained. Finally, SEM imaging and analysis confirmed the targeted pore interconnectivity and ~220 mm average pore size, within the range associated with osteogenesis. Porosity calculations revealed that all scaffolds were similarly ~60%.

Scaffold Thermal Properties

PCL $T_m$. The midpoint melting temperature of PCL ($T_{m,PCL}$) represents the temperature to which the scaffold must be heated to confer maximum shape recovery, key to self-fitting into the bone defect. The $T_m$ values were quantified for all scaffold compositions. Table 3 below illustrates thermal properties of the scaffolds.

TABLE 3

Thermal properties

| | PCL | | | PLLA | | |
|---|---|---|---|---|---|---|
| | $T_m$ onset (° C.) | $T_m$ midpoint (° C.) | % Crystallinity | $T_m$ onset (° C.) | $T_m$ midpoint (° C.) | % Crystallinity |
| LPCL | 50.5 ± 0.41 | 56.1 ± 0.56 | 42.7 ± 1.7 | — | — | — |
| L/L | 50.5 ± 0.61 | 56.6 ± 0.21 | 42.0 ± 1.9 | 153.9 ± 1.8 | 164.0 ± 1.5 | 37.6 ± 7.3 |
| L/S | 51.1 ± 0.27 | 56.3 ± 0.25 | 42.5 ± 2.0 | 152.2 ± 0.84 | 157.5 ± 0.44 | 19.5 ± 1.8 |
| SPCL | 42.6 ± 0.20 | 49.2 ± 0.02 | 30.4 ± 3.5 | — | — | — |
| S/L | 41.0 ± 0.83 | 50.0 ± 0.12 | 33.5 ± 1.6 | 155 ± 0.56 | 160.0 ± 0.19 | 23.0 ± 7.1 |
| S/S | 39.7 ± 2.0 | 50.3 ± 0.20 | 39.2 ± 4.3 | 147.9 ± 2.2 | 156.5 ± 0.13 | 24.7 ± 5.8 |

Figure 1B:
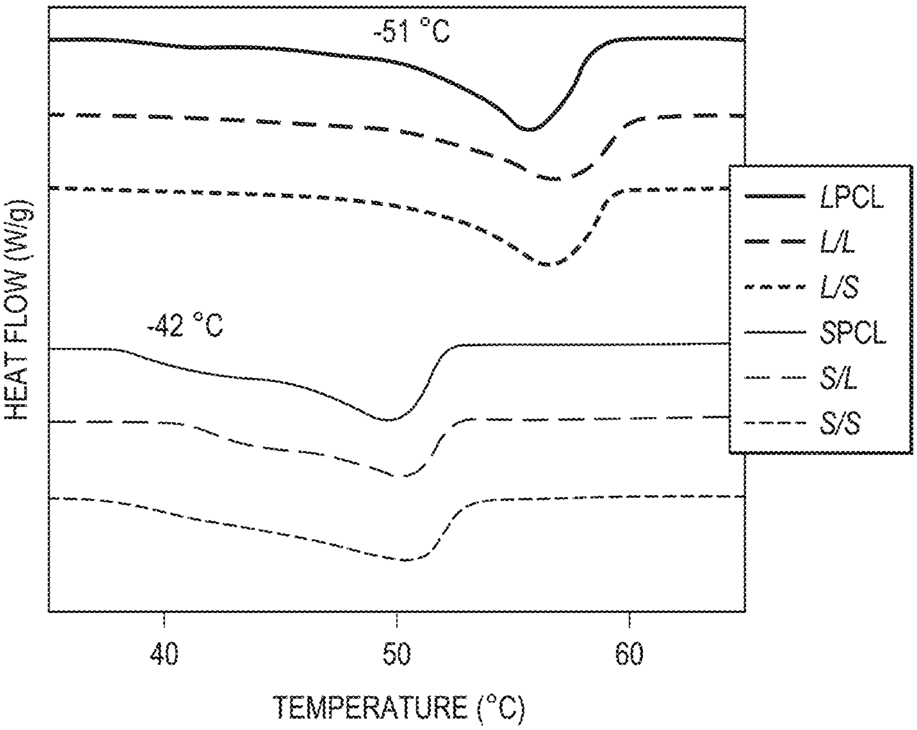
FIG. 1**(B) Representative thermogram for each scaffold composition.

Notably, the midpoint $T_{m,PCL}$ values were significantly reduced (~6° C.) for star-PCL-based versus linear-PCL-based scaffolds. The LPCL scaffold had a $T_{m,PCL}$~56° C. (midpoint) that was maintained following incorporation of linear- or star-PLLA to form L/L and US semi-IPN scaffolds, respectively. In contrast, for the SPCL scaffold, the $T_{m,PCL}$ (midpoint) was significantly reduced to ~50° C. These values were maintained with the incorporation of linear- or star-PLLA to form S/L and S/S semi-IPNS, respectively. As is discussed later, star-PCL-based scaffolds begin to soften and undergo self-fitting in model defects at temperatures below $T_{m,PCL}$~50° C. (midpoint), due to the fact that the onset melting temperature of PCL is just ~42° C. (FIG. 1B). This presented a unique way to afford a tunable $T_{m,PCL}$ in a chemically cross-linked PCL scaffold. In contrast, linear PCL $M_n$ (~10 kg $mol^{-1}$ and ~5 kg $mol^{-1}$) were previously tuned, but this did not yield appreciable differences in scaffold $T_{m,PCL}$ (56.2±0.4 and 54.4±0.6° C., respectively). In this way, star-PCL-based compositions are expected to improve tissue safety during self-fitting into bone defects.

PCL crystallinity. PCL crystalline lamellae are the origin of shape memory behavior, and self-fitting behavior, and further have a significant impact on degradation and mechanical properties. Thus, scaffold PCL % crystallinity was quantified from DSC (Table 3). For LPCL, PCL % crystallinity was ~42%. When corrected for weight % in semi-IPN compositions (PCL/PLLA, 75/25 wt %), PCL % crystallinity was maintained for linear-PCL-based semi-IPNs (i.e., L/L and US). In the case of SPCL, PCL crystallinity was significantly reduced to ~30%. As described later, the PCL % crystallinity of all scaffolds was sufficient to retain similarly shape recovery and shape fixity. However, the addition of linear- or star-PLLA to form S/L and S/S semi-IPNs resulted in increased PCL crystallinity of ~34% and ~39% (with S/S similar to the LPCL control), respectively.

PLLA crystallinity. PLLA crystallinity can also impact scaffold degradation and mechanical properties. The previously reported L/L semi-IPN scaffold exhibited PLLA crystallinity (~38%) and $T_{m,PLLA}$ (midpoint) (164° C.) (Table 3). When star-PLLA was incorporated into the linear-PCL-DA network, the resulting S/L semi-IPN scaffold exhibited significantly decreased PLLA crystallinity (~20%, ~158° C.). For star-PCL-based semi-IPNs, the PLLA crystallinity was somewhat intermediate: S/L (~23%, ~160° C.) and S/S (~25%, ~157° C.), but was not statistically significant compared to the L/L. Thus, versus the L/L semi-IPN scaffolds, the S/L, S/L, and S/S had somewhat diminished PLLA crystallinity and is considered in analysis of degradation and mechanical properties.

Figure 2A:
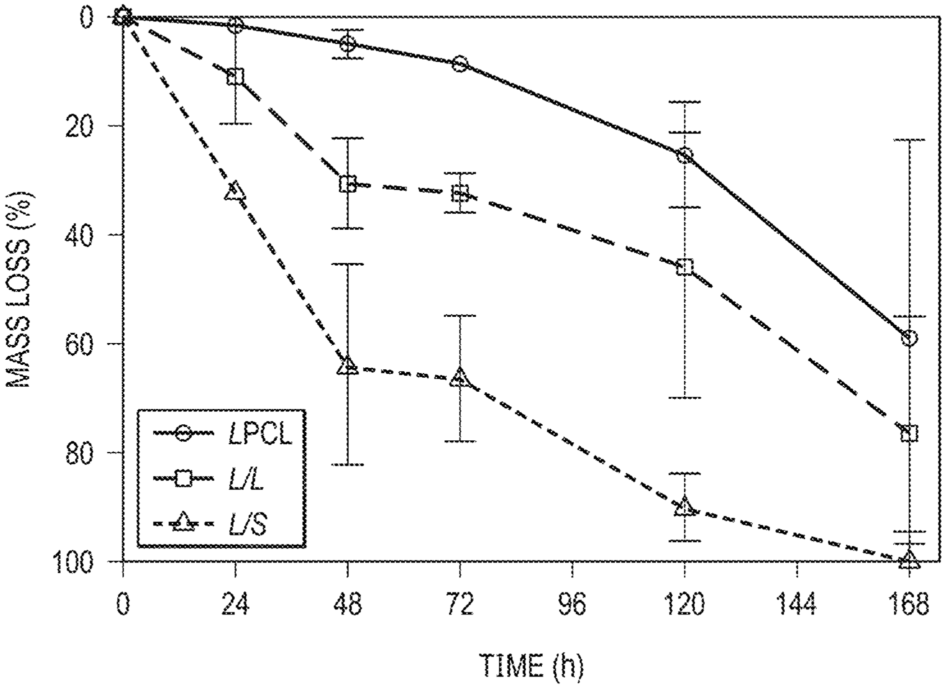
FIGS. 2(A)-2(C) illustrate gravimetric mass loss over time for base-catalyzed degradation studies (0.2 M NaOH, 37° C., 60 rpm).
Figure 2B:
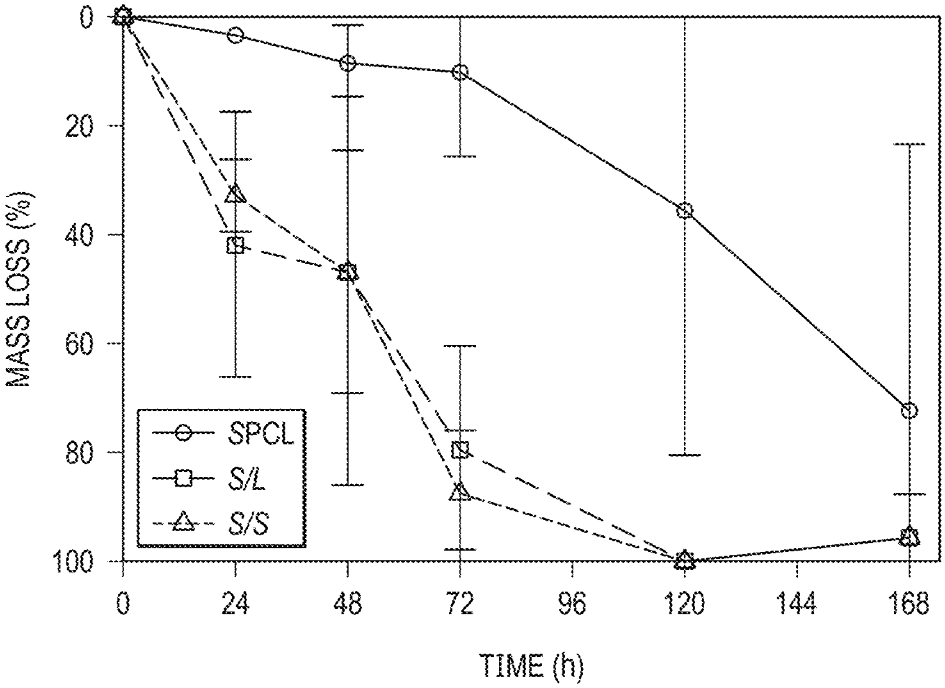
Figure 2C:
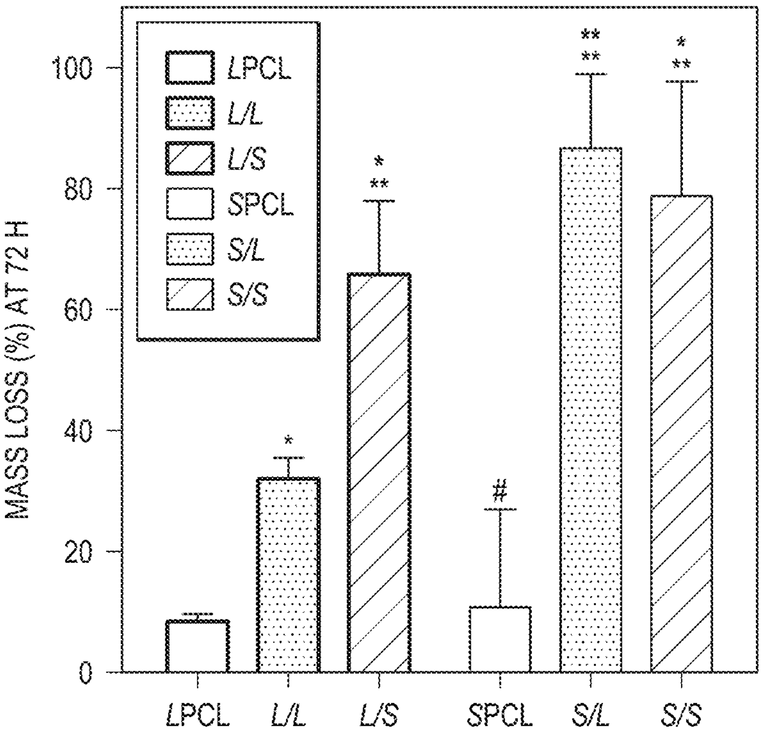

Degradation behavior. Previously, it was reported that the L/L semi-IPN scaffold degraded significantly faster than the LPCL control. Further acceleration of degradation is anticipated to favorably allow neotissue formation as well as osteogenesis. The present disclosure revealed that the US semi-IPN degraded faster than the L/L semi-IPN (FIG. 2A). In the case of star-PCL-based compositions, the SPCL scaffold degraded slowly, similar to LPCL (FIG. 2B). However, the S/L and S/S semi-IPNs degraded faster and generally similar to each other. By examining mass loss at the 72 h timepoint (FIG. 2C) as well as images of specimens at increasing time points, it is clear that S/L and S/S exhibited the most rapid rate of mass loss, even faster than US. Notably, mass loss at earlier timepoints (48 h) was greater for S/S versus S/L. While reduced levels of PCL and/or PLLA % crystallinity of semi-IPNs (Table 3) would be predicted to increase their rate of degradation, these properties were not always correlative. For instance, the US and S/S showed similar PCL % crystallinity (~40%), and the US showed a lower PLLA % crystallinity (~20% compared to 25%), but the S/S degraded significantly faster than the L/S. Thus, PCL/PLLA phase separation was considered, as this has been known to contribute to accelerated degradation of blends and semi-IPNs. SEM of analogous solid films demonstrated distinct morphologies for each composition. Both 100% PCL controls [LPCL and SPCL] showed a uniform morphology as expected based on their chemical homogeneity. The UL (i.e., slowest degrading semi-IPN) also showed minimal signs of phase separation. However, all other semi-IPNs [L/S, S/L and S/S] showed greater evidence of coalescence, indicative of greater phase separation or immiscibility. Further, these new semi-IPN scaffolds demonstrate the potential to both accelerate and tune scaffold degradation rates based on phase separation. The current results were limited to base-catalyzed conditions, known to impact polyester degradation kinetics. Thus, future studies wherein scaffold degradation is assessed in vitro under physiological conditions as well as in vivo would be informative. PCL has been known to degrade in vivo over the course of ~2 years, but these faster degrading scaffolds are expected to more closely mimic the timescale of CMF bone regeneration (3 to 6 months). As rates of regeneration can vary due to patient age and other factors, the tunability of these scaffolds' degradation rates may be advantageous.

Mechanical, Shape Memory, and Radial Expansion Pressure Properties

Figure 3A:
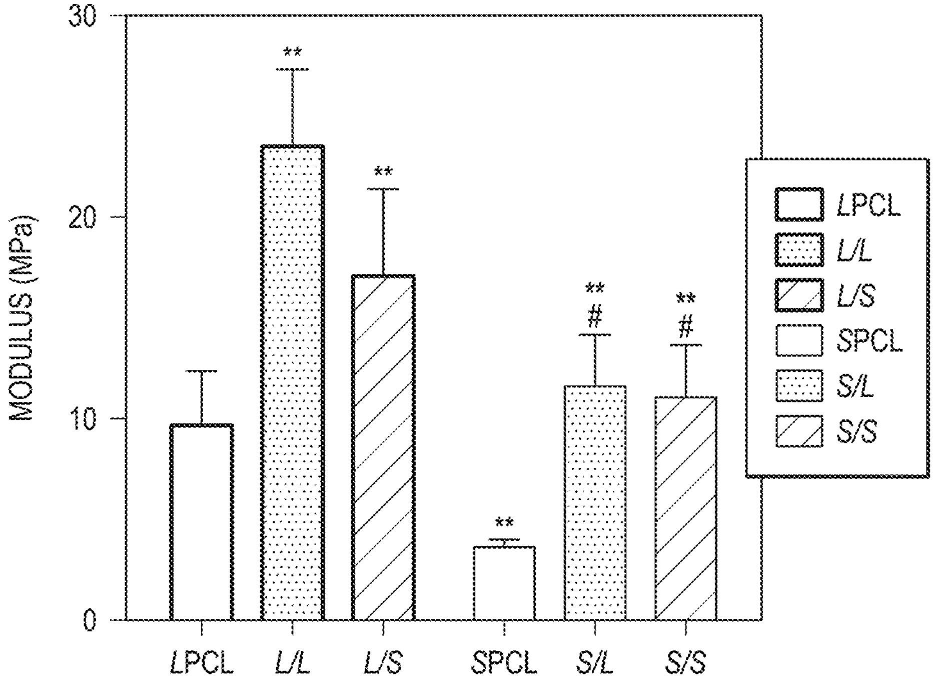
FIGS. 3(A)-3(C) Compressive mechanical properties were compared including 3(A) Modulus of Elasticity (MPa), 3(B) Compressive Strength (MPa), and 3(C) toughness (mJ); *p<0.05, **p<0.01, #p>0.05.

Mechanical properties. Mechanically robust SMP scaffolds are expected to afford superior outcomes in the treatment of bone defects. Static compressive testing was performed to assess the mechanical properties of the SMP scaffolds. For linear-PCL-based compositions, versus the LPCL control (~9.65 MPa), the modulus (E) was significantly increased for both the L/L (~23.8 MPa) and L/S (~17.4 MPa) semi-IPNs (FIG. 3A and Table 4).

TABLE 4

Mechanical properties of scaffolds

| | Modulus (MPa) | Compressive Strength (MPa) | Toughness (mJ) |
|---|---|---|---|
| LPCL | 9.65 ± 2.8 | 21.6 ± 4.0 | 238 ± 74 |
| L/L | 23.8 ± 3.6 | 28.0 ± 5.2 | 275 ± 66 |
| L/S | 17.4 ± 4.2 | 34.3 ± 6.0 | 325 ± 61 |
| SPCL | 3.57 ± 0.58 | 15.0 ± 3.2 | 115 ± 25 |
| S/L | 11.9 ± 2.3 | 24.5 ± 7.7 | 184 ± 45 |
| S/S | 11.3 ± 2.4 | 15.3 ± 6.8 | 138 ± 58 |

Figure 3B:
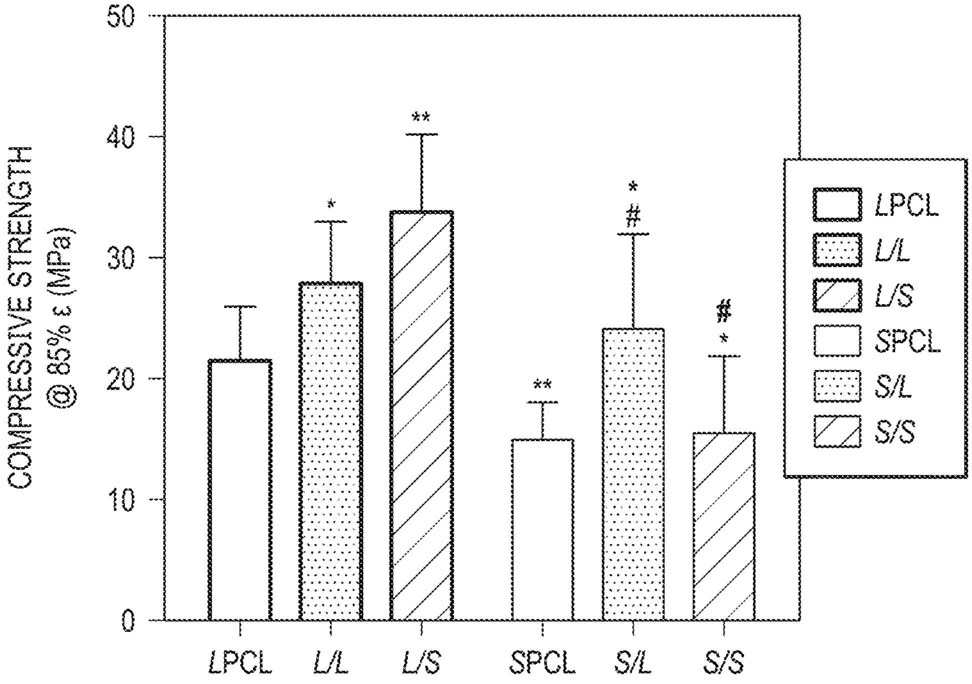
Figure 3C:
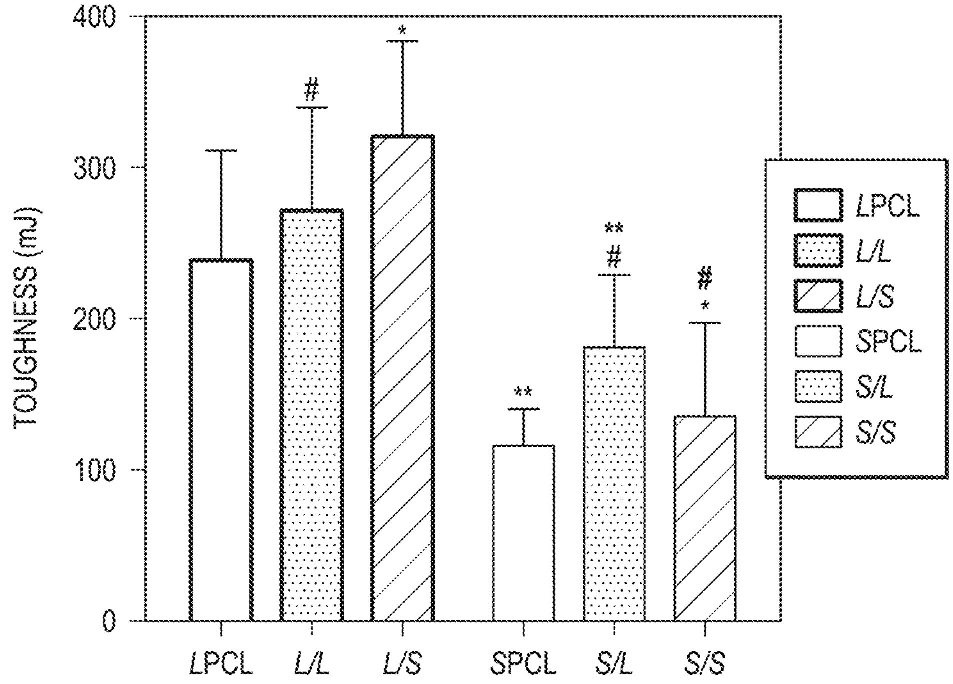

In terms of star-PCL-based compositions, for the SPCL control (~3.57 MPa), E was significantly lower than the LPCL. This was attributed to the former's reduced PCL % crystallinity, in spite of having a higher relative cross-link density. However, versus the SPCL, E was increased for the S/L (~11.9 MPa) and S/S (~11.3 MPa) semi-IPNs, similar to the LPCL control. All semi-IPNS exhibited higher E values versus the 100% PCL controls, but the E values of L/L and L/S were higher than that of S/L and S/S. Similar trends generally emerged for compressive strength (CS) (FIG. 3B) as well as for toughness (FIG. 3C). No scaffold fractured during the test (i.e. withstood 85% strain), indicative of their non-brittle behavior that is desirable in the intended application of CMF bone defect treatment. Moreover, all scaffold compositions demonstrated robust mechanical properties for handling and press-fitting. Of all compositions, the L/S semi-IPN exhibited the greatest CS and toughness, while the S/L semi-IPN exhibited enhanced CS and toughness versus the SPCL control. Thus, a star-architecture affords certain semi-IPNs (L/S and S/L) with particularly notable mechanical properties.

Self-fitting properties. Scaffold specimens (d~6 mm×t~2 mm) were press-fitted into a plastic model defect (d~5 mm×t~2 mm). This defect represented a rat bilateral calvarial defect model of the same dimensions, typically used as an entry-level model for bone defect healing studies. A slighter larger scaffold diameter was selected to promote contact along the defect perimeter. Herein, scaffolds were fitted in the same fashion envisioned a clinical setting. A $T_{fit}$ was the minimum saline bath temperature that in just 1 minute produced a softened, malleable scaffold: ~55° C. for linear-PCL-based and ~45° C. for star-PCL-based scaffolds. A sequence of steps was used to assess self-fitting and ultimately quantify $R_f$ and $R_r$. Following submersion in saline at $T_{fit}$ for 1 minute [step 1], all scaffolds were successfully press-fitted into defects (i.e. expanded via shape recovery to fill the defect) [step 2]. After just 2 minutes within the defect, scaffolds returned to their relatively rigid state (i.e. underwent shape fixation in new shape within the defect) [step 3]. Next, scaffolds were removed from the defect and allowed to sit for 2 min (to determine shape fixity) [step 4] and reheated at $T_{fit}$ in saline for 1 minute (to determine shape recovery) [step 5]. For both cycles, these values were consistently at or near 100% for all scaffolds. These results further validate that the semi-IPN design, based on any combination of linear-PCL-DA or star-PCL-TA and both linear-PLLA or star-PLLA, does not compromise shape memory behavior. However, as osteonecrosis begins to occur with exposure to temperatures≥50° C., the lower $T_{fit}$ of star-PCL-based scaffolds (i.e. SPCL, S/L, and S/S) is more "tissue-safe". Furthermore, the observed $T_{fit}$ of 45° C. is considered ideal for self-fitting CMF bone scaffolds, as it is sufficiently above $T_{body}$ and so exists in a rigid state within the defect to support healing.

Figure 4:
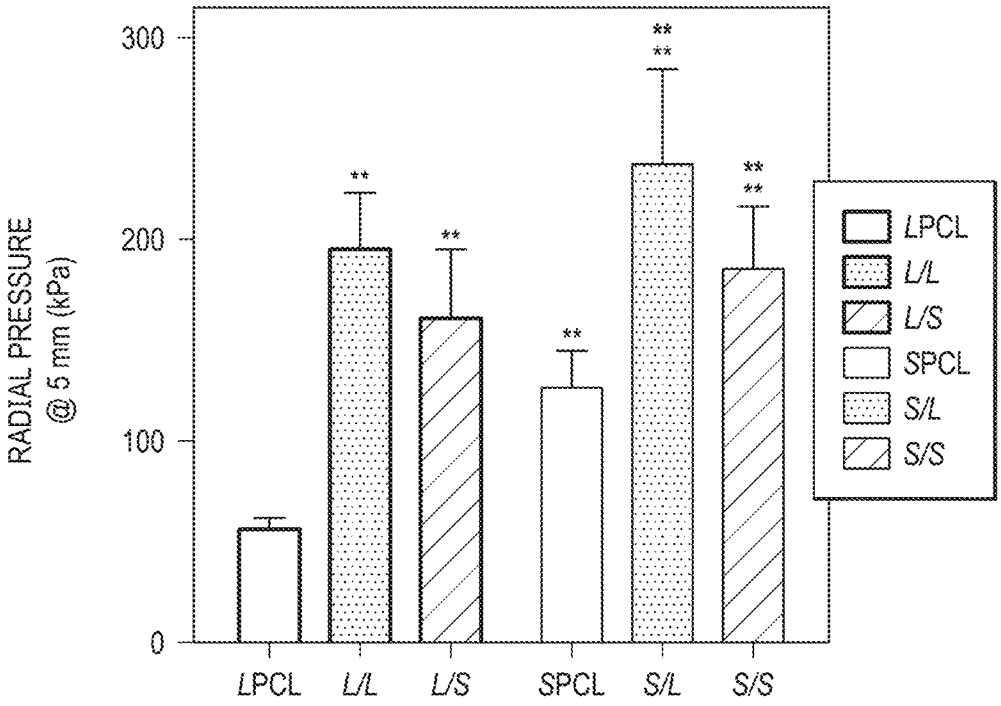
FIG. 4 Shape memory testing was performed to mimic a bilateral rat calvarial defect model in vivo study.

Radial pressure. For the first time, the radial pressures exerted by the SMP scaffolds during self-fitting at their $T_{fit}$ to quantify the force exerted by the scaffold against the defect edges, driven by shape recovery (FIG. 4) is reported. The pressure was monitored while a scaffold (d~6 mm×t~2 mm), initially loaded into a bore (d~6.5 mm) at RT, was heated to its $T_{fit}$ and the bore diameter then reduced to that of a calvarial defect (d~5 mm). Versus the LPCL control (~57 kPa), radial pressure significantly increased for the L/L (~195 kPa) and L/S (~162 kPa) semi-IPNs, attributed to the rigid PLLA. The radial pressure of the SPCL (~127 kPa) was also much higher than the LPCL, which may be attributed to its higher crosslink density. A further substantial increase in radial pressure was noted for the S/L (~239 kPa) and S/S (~188 kPa) versus the SPCL, again stemming from the rigid PLLA. Thus, the substantial gains in radial pressure (versus the LPCL control) observed for the SPCL and all semi-IPNs affords improved scaffold expansion toward defect edges during self-fitting, which is anticipated to promote osseointegration and overall implant stability in vivo.

Solution Viscosity and Scaffold Scale-Up

Figure 5A:
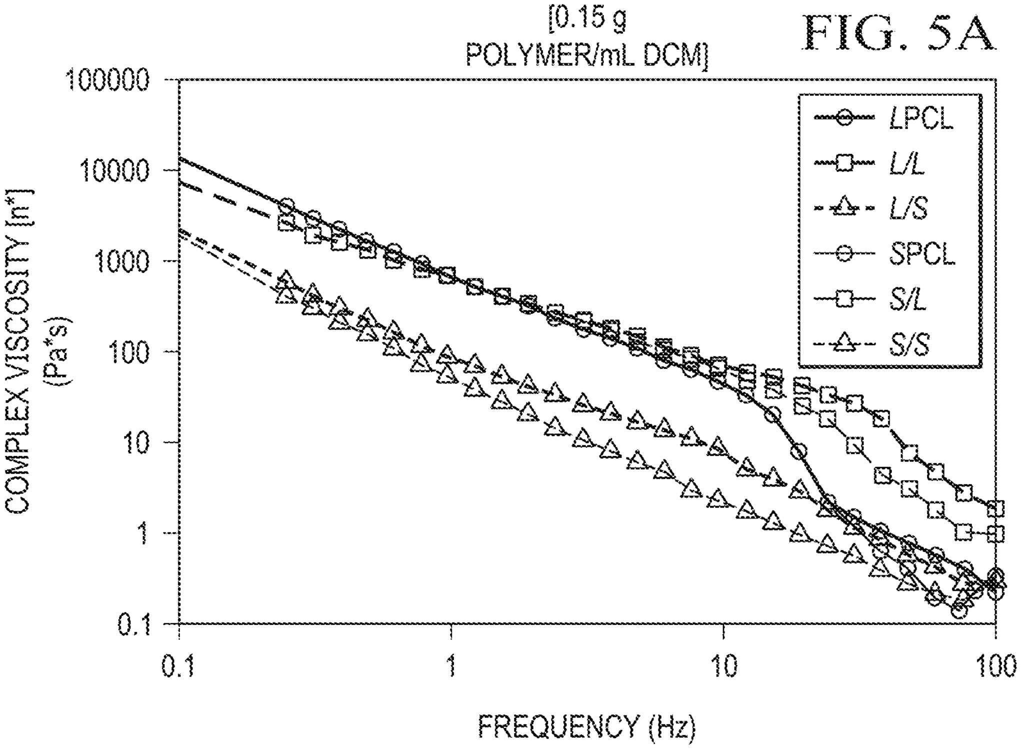
FIGS. 5(A) and 5B illustrate complex viscosity [Z*] versus frequency and intrinsic viscosity (*p<0.05, **p<0.01 compared to LPCL), respectively, for scaffold precursor solutions.
Figure 5B:
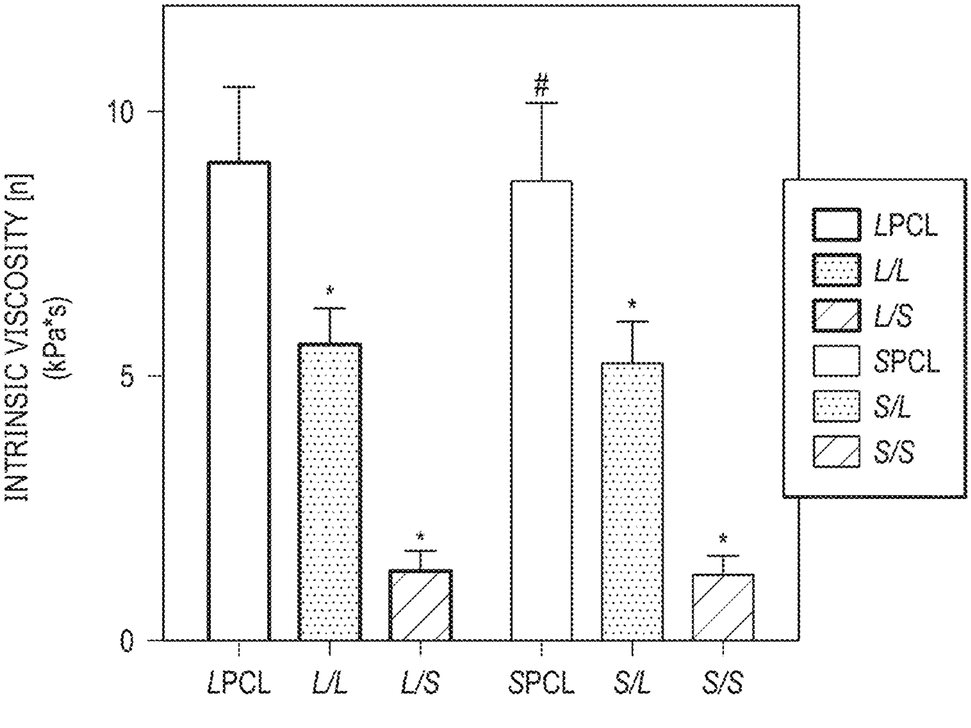

In the aforementioned analyses, SMP scaffolds were prepared with a diameter of ~6 mm (biopsy punch of a scaffold with d~12 mm); this size is appropriate for bilateral rat calvarial defect studies. However, larger scaffolds are necessary for critically-sized defects in animal models (up to d~22 mm) and eventually for human patients. While centrifugation to drive diffusion is permissible for small scaffolds that are prepared in scintillation vials, this is not the case for larger scaffolds. Because star-polymers are known to have a lowered solution viscosity, it was expected that SMP scaffolds prepared with such would more readily permit the preparation of larger specimens. First, the complex viscosity [Z*] of scaffold precursor solutions were determined over a frequency sweep (FIG. 5A) and the intrinsic viscosity calculated by extrapolation to a zero-shear rate (FIG. 5B). Both 100% PCL controls (LPCL and SPCL), exhibited a relatively high intrinsic viscosity (~9 kPa*s). For semi-IPN macromer solutions containing linear-PCL, intrinsic viscosity was reduced with star-PLLA (L/S; ~1 kPa*s) versus with linear-PLLA (L/L; ~6 kPa*s). Semi-IPN macromer solutions based on star-PCL were likewise reduced, particularly with star-PLLA (S/S; ~1 kPa*s) versus with linear-PLLA (S/L; ~6 kPa*s). Because of their relatively high and low intrinsic viscosities, respectively, L/L and S/S semi-IPN macromer solutions were selected to prepare larger scaffold specimens. First, using fused salt templates prepared in scintillation vials, diffusion of the precursor solutions containing food coloring was monitored. Owing to its lower intrinsic viscosity, the S/S solution diffused more quickly to the bottom of the template (~90 s) versus the L/L solution (4120 s). Next, L/L and S/S were prepared as actual scaled-up, "larger" scaffolds, using 100 mL beakers (50.0 g salt). Analogous "regular" scaffolds were prepared in the 20 mL vials (10.0 g salt), but the diameter was not reduced from ~12 mm using a biopsy punch. Thus, the "larger" scaffolds had a diameter and volume that was 2× and 5×, respectively, that of the "regular" scaffolds. For the "large" S/S scaffolds, a total of four 2 mm thick specimens (i.e. slices) could be harvested versus just three 2 mm thick slices for the "larger" L/L scaffolds. This stemmed from a lack of diffusion, wherein the L/L macromer solution did not reach the bottom of the mold, rendering the bottom portion deficient. While density did not change according to gravimetric analysis, low magnification optical microscopy revealed that S/S demonstrated superior uniformity of pores throughout versus the L/L. Full porogen leaching has been previously noted as a limitation in SCPL fabrication; however, herein the NaCl porogen used in fabrication was shown to be fully removed even from "larger" scaffolds, likely owing to the use of a fused salt template resulting in interconnected pores. This was validated via SEM and EDS mapping to show that the scaffolds did not contain any appreciable amount of Na or Cl. Lastly, as a further indicator of their utility as a surgical product to treat bone defects, the S/S scaffold was able to be trimmed with a scissor and also sutured.

Working Example lPCL-DA ("linear" architecture) and ★PCL-TA ("star" architecture) macromomers of varying molecular weight ($M_n$) were prepared and used to fabricate scaffolds via solvent casting particulate leaching (SCPL) with a fused salt template. Scaffolds formed with ★PCL-TA exhibited reduced % PCL crystallinity, and hence reduced $T_m$ values, relative to those formed with lPCL-DA. $T_m$ (and % crystallinity) systematically decreased as the $M_n$ of the ★PCL-TA was decreased. In this way, a scaffold prepared from PCL-TA ($M_n$~10 k g mol$^{-1}$), PCL-TA ($M_n$~7.5 k g mol$^{-1}$), and PCL-TA ($M_n$~5 k g mol$^{-1}$) exhibited a $T_m$'s of ~29° C. and so would expand ("shape recovery") upon insertion. In addition to "PCL-only" scaffolds, this approach could be used to form PCL/PLLA scaffolds with reduced $T_m$ by combining ★PCL-TA (rather than lPCL-DA) with PLLA as described in other prior examples.

PCL (diol and tetrol) were prepared via ring-opening polymerization (ROP) of ε-caprolactone using an alcohol initiator (ethylene glycol or pentaerythritol, respectively) and stannous octoate as the catalyst. Molecular weight ($M_n$=10 k, 7.5 k, and 5 k g mol$^{-1}$) was modulated via ε-caprolactone to initiator ratio. Six macromer compositions were created: 10 k l (lPCL-DA, $M_n$~10 k g mol$^{-1}$), 7.5 k l (lPCL-DA, $M_n$~7.5 k g mol$^{-1}$), 5 k l (lPCL-DA, $M_n$~5 k g mol$^{-1}$), 10 k★ (★PCL-TA, $M_n$~10 k g mol$^{-1}$), 7.5 k★ (★PCL-TA, $M_n$~7.5 k g mol$^{-1}$), and 5 k★ (★PCL-TA, $M_n$~5 k g mol$^{-1}$).

SMP scaffolds were fabricated using solvent cast particulate leaching protocols to achieve porous scaffolds. NaCl was sieved and portioned into 20 mL scintillation vials (10.0 g, 425 um). DI water (7.5 wt %) was added in four additions followed by manual stirring after each addition. The wet salt was then compacted together using a glass stir rod and the vials were centrifuged (15 min, 3220×g). The vials were then air-dried for ~1 hour and vacuum dried (RT, ON, 30 in. Hg). Macromer solutions were prepared by dissolving the desired macromer in DCM at 100 wt % (0.15 g total per mL DCM). Photoinitiator solution (10 wt % DMP in NVP) was then added at 15 vol %. To each salt template, 5 mL of the photoinitiator solution combined with the macromer solution were added and subsequently centrifuged (10 min, 1260×g). To crosslink the acrylated macromer solutions, vials were opened and exposed to UV light (UV-Transilluminator, 6 mW cm$^2$, 365 nm) for 6 min then left in the fume hood to air dry ON. To leach he salt from the scaffolds, vials were placed in a 1:1 ratio of water to ethanol for ~5 days with daily solution changes. Once all the salt was dissolved out, scaffolds were left to dry in the fume hood ON and heat-treated the next day (85 C, 1 hr min, 30 in. Hg). The dried scaffolds (d×12 mm) were sliced into three specimens (t×2 mm) (Vibratome, Leica VT 1000 S) and were biopsy punched (Integra Miltex, 6 mm). The final specimen dimensions were d~6 mm×t~2 mm.

Thermal Properties. Differential Scanning Calorimetry (DSC; TA Instruments Q100) was used to determine $T_m$, $T_{onset}$, and % Crystallinity of the PCL prior to scaffold fabrication and once fabricated into scaffolds (~10 mg; N=3). Each specimen was sealed in hermetic pans and heated/cooled (10° C. min$^{-1}$) in two cycles. Reported values were determined using the second cycle to account for removal of thermal history in the polymers. The onset and midpoint temperatures were determined using TA Universal Analysis software where the maximum endothermic melt peak was analyzed to get the thermal properties as well as enthalpy of fusion. Percent crystallinity was calculated using equation (6):

$$\% \ X_c = \frac{\Delta H_m - \Delta H_c}{\Delta H_c^{\circ}} \tag{6}$$

Where $\Delta H_m$ is the enthalpy of fusion calculated from the integral of the endothermic melt peak, $\Delta H_c$ is the enthalpy of crystallization from the exothermic cold crystallization peak and $\Delta H^o_c$ is the theoretical value for 100% crystalline PCL (139.5 Jg$^{-1}$). These results demonstrate the ability to create scaffolds with tunable $T_m$ values (i.e., shape recovery temperatures) using ★PCL-TA macromers of varying $M_n$ values.

Compressive Properties. Scaffold specimens (d~6 mm×t~2 mm; N=5) underwent static compression testing (Instron 5944) at RT. Specimens were subjected to a constant strain (1.5 mm min$^{-1}$) up to 85% strain. Due to their non-brittle nature, no specimen fractured. The average compressive modulus (E), strength (CS), and toughness were reported: E was determined from the initial linear region (<10% e). CS was determined from the stress at 85% strain. Toughness values were calculated from the area of the stress-strain curves up to 85% strain. These results demonstrate the reduction in compressive mechanical properties as PCL crystallinity is reduced.

Accelerated Degradation. Specimens (d~6×t~2 mm; N=3 per timepoint) were submerged in 10 mL of 0.1 M NaOH in a 20 mL glass scintillation vials. Samples were placed in an incubator (37° C. and 60 rpm). This study was conducted over 18 days with daily timepoints removed, rinsed with DI water, and dried in vacuo (RT; ON; 36 in. Hg). The final dried mass was compared to the initial mass to determine the mass loss (%). These results demonstrate the reduction that scaffolds with faster rates of degradation are produced when prepared from ★PCL-TA macromers ($M_n$~7.5 k and 5 k g mol$^{-1}$).

Pore Size. SEM (Tescan Vega 3, Au—Pt sputter coating (—4 nm), accelerating voltage ~10 kV) was used to analyze and visualize pore morphology. Scaffold images (N=3) were analyzed using image analysis software (ImageJ) and measurements were taken from pores along the diagonal midline to determine the average pore size.

Porosity. The percent porosity of scaffolds was determined by weighing and measuring the dimensions of films and porous scaffolds by using equation (7):

$$\text{Porosity } (\%) = \rho \frac{\rho_{solid\ film} - \rho_{porous\ scaffold}}{\rho_{solid\ film}} * 100 \tag{7}$$

Where $\rho_{porous\ scaffold}$ is the density of the final scaffold specimens and $\rho_{solid\ film}$ is the density of the corresponding solid film.

Pore Interconnectivity. Scaffolds (N=3; 6 mm diameter) were evaluated to determine their pore interconnectivity using a water wicking procedure. Scaffolds were submerged in 10 mL DI water and placed on a shaker plate (150 rpm, 24 hrs). Swollen scaffolds were removed and weighed on a petri dish. A folded Kimwipe was gently pressed onto the surface of the scaffolds for 1 min to wick away the interconnected water ($Mass_{total}$) The scaffold was then weight again to get the $Mass_{interconnected}$ using equation (8):

$$\text{Interconnectivity (\%)} = \frac{Mass_{total} - Mass_{interconnected}}{Mass_{total}} * 100 \quad (8)$$

These results demonstrate the reduction that porous scaffolds with pore interconnectivity can be prepared from lPCL-DA ("linear" architecture) and ★PCL-TA ("star" architecture) macromomers.

TGA of solid films was performed to verify crosslinking within the films and to analyze thermal degradation rates for linear-PCL-DA compositions and star-PCL-TA compositions. The results demonstrated that scaffolds prepared from lPCL-DA ("linear" architecture) and ★PCL-TA ("star" architecture) macromomers are effectively crosslinked, due to the lack of significant weight loss prior to catastrophic weight loss (~400° C.).

TABLE 5

| Shape memory cycle data - cycle 2 | | |
|---|---|---|
| | $R_{F\ CYCLE\ 2}$ | $R_{R\ CYCLE\ 2}$ |
| 10Kl | 101.92 ± 3.62 | 96.98 ± 1.90 |
| 10K★ | 103.48 ± 4.16 | 96.42 ± 1.02 |
| 7.5Kl | 102.28 ± 2.62 | 101.33 ± 3.46 |
| 7.5K★ | 102.68 ± 5.52 | 101.18 ± 4.19 |
| 5Kl | 95.25 ± 3.12 | 99.67 ± 1.64 |
| 5K★ | 105.43 ± 2.28 | 91.37 ± 5.49 |

The results in Table 5 demonstrate that scaffolds prepared from lPCL-DA ("linear" architecture) and ★PCL-TA ("star" architecture) macromomers exhibit excellent shape fixity (Rf) and shape recovery (Rr).

CONCLUSIONS

Towards improving the utility of "self-fitting" SMP scaffolds, semi-IPN compositions were prepared with star-polymer architectures. Originally prepared from linear-PCL-DA and linear-PLLA (75/25 wt %), the L/L semi-IPN exhibited improved rigidity and accelerated degradation versus linear-PCL-DA (LPCL). In the present disclosure, the semi-IPN based on star-PCL-TA and star-PLLA (S/S) (75/25 wt %) exhibited distinct advantages and fulfilled key criteria as a surgical product to treat CMF and other bone defects. The pore size (~220 mm) and pore interconnectivity, to promote osteogenesis and to favorably allow neotissue infiltration, was maintained using the SCPL fabrication protocol. While this study was limited to in vitro material characterization, the LPCL control scaffold had been previously shown to support osteogenesis, which was improved with the addition of cell adhesion motifs and bioactive coatings. The new scaffold compositions are expected to yield favorable and potentially improved results in such cell culture studies. Importantly, self-fitting of the S/S semi-IPN scaffold could be performed at a more tissue-safe, lower $T_{fit}$ (~45° C.) versus for the L/L semi-IPN scaffold (~55° C.). The S/S semi-IPN exhibited similar rigidity versus the original LPCL, although it was somewhat less rigid and strong versus the L/L semi-IPN. Despite this, radial pressure during shape recovery at $T_{fit}$ for the S/S semi-IPN was shown to be significantly improved versus for the LPCL and was similar to that of the L/L semi-IPN. This ability to expand with greater force toward the defect edges during self-fitting is expected to improve scaffold osseointegration and implant stability prior to healing. Additionally, the S/S semi-IPN exhibited even faster degradation versus the L/L semi-IPN, and so is expected to better promote neotissue infiltration. Finally, the reduced intrinsic viscosity of S/S semi-IPN precursor solution improved its diffusion through the salt template (in the absence of centrifugation), permitting larger scaffolds to be prepared. Thus, star-polymer architectures were successfully leveraged to create "self-fitting" SMP scaffolds with properties better suited for treatment of CMF bone defects and other bone defects.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

Conditional language used herein, such as, among others, "can", "might", "may", "e.g.", and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

Although various embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth herein.

What is claimed is:

1. A shape memory polymer (SMP) scaffold, the SMP scaffold comprising:

at least one macromer or a polymer, wherein the at least one macromer or polymer comprises a star configuration, and a photoinitiator to crosslink the at least one macromer or polymer.

2. The SMP scaffold of claim 1, wherein the at least one macromer or polymer is selected from the group consisting of linear-poly(ε-caprolactone)-diacrylate (linear-PCL-DA), linear-PCL, star-PCL-tetraacrylate (star-PCL-TA), and star-PCL and optionally combined with one or more macromer or polymer selected from the group consisting of linear-poly (L-lactic acid) (linear-PLLA), star-PLLA (star-PLLA), natural polymers, synthetic polymers, semi-synthetic polymers, copolymers, other polyesters, polyolefins, polyvinyls, or other polymers, derivatives thereof, combinations thereof, and macromers only compositions.

3. The SMP scaffold of claim 1, wherein the photoinitiator is formed via a solution of 2,2-dimethoxy-2-phenyl acetophenone (DMP) in 1-vinyl-2-pyrrolidinone (NVP).

4. The SMP scaffold of claim 1, wherein the at least one macromer comprises star-PCL-TA macromers and/or linear-PCL-DA, and wherein the SMP scaffold further comprises semi-interpenetrating networks (semi-IPNs) with cross-linked linear-PCL-DA and star-PCL-TA.

5. The SMP scaffold of claim 1, further comprising at least one of exogenous cells, growth factors, bioglass, tricalcium phosphate, hydroxyapatite, silicates or other fillers, composites, or combinations thereof.

6. The SMP scaffold of claim 1, further comprising a coating.

7. The SMP scaffold of claim 1, wherein a Tm (i.e., Ttrans) of the SMP scaffold is tuned via use of a star-PCL macromer or polymer.

8. The SMP scaffold of claim 7, wherein the Tm of the SMP scaffold is tuned to body temperature or below, permitting expansion upon implantation.

9. The SMP scaffold of claim 7, wherein tuning of the SMP scaffold via use of a star-PCL allows for application in a defect of a subject without use of warm saline, other fluid, or air for application.

10. The SMP scaffold of claim 7, wherein tuning of the Tm of the SMP scaffold via use of a star-PCL to <55° C. allows for implantation in a defect by heating to <55° C. using at least one of water, saline, buffer, air, or the like.

11. The SMP scaffold of claim 1, wherein the SMP scaffold is formed via a method selected from the group consisting of solvent-casting/particulate leaching (SCPL), electrospinning, additive manufacturing, and combinations thereof.

* * * * *